(12) United States Patent
Gur

(10) Patent No.: US 9,816,627 B2
(45) Date of Patent: Nov. 14, 2017

(54) VARIABLE ORIFICE ROTARY VALVES FOR CONTROLLING GAS FLOW

(75) Inventor: Ory Gur, Newport Coast, CA (US)

(73) Assignee: Origin Medical Devices Inc., Newport Coast, CA (US)

( * ) Notice: Subject to any disclaimer, the term of this patent is extended or adjusted under 35 U.S.C. 154(b) by 482 days.

(21) Appl. No.: 13/985,198

(22) PCT Filed: Feb. 14, 2012

(86) PCT No.: PCT/US2012/025062
§ 371 (c)(1),
(2), (4) Date: Aug. 13, 2013

(87) PCT Pub. No.: WO2012/112562
PCT Pub. Date: Aug. 23, 2012

(65) Prior Publication Data
US 2013/0334446 A1   Dec. 19, 2013

Related U.S. Application Data

(60) Provisional application No. 61/442,915, filed on Feb. 15, 2011.

(51) Int. Cl.
*F16K 5/04* (2006.01)
*F16K 5/10* (2006.01)
(Continued)

(52) U.S. Cl.
CPC .......... *F16K 11/085* (2013.01); *F16K 5/0414* (2013.01); *F16K 5/103* (2013.01);
(Continued)

(58) Field of Classification Search
CPC .... F16K 11/085; F16K 5/103; F16K 37/0041; F16K 5/0414; F16K 37/0033; A61M 16/0825; A61M 16/205; A61M 16/0045
See application file for complete search history.

(56) References Cited

U.S. PATENT DOCUMENTS

| 743,714 A | * | 11/1903 | Guese | F16K 11/074 137/625.11 |
| 2,100,366 A | * | 11/1937 | Tyler | F16K 3/085 137/625.31 |

(Continued)

FOREIGN PATENT DOCUMENTS

DE   102008056075 A1   5/2010

*Primary Examiner* — Mary McManmon
*Assistant Examiner* — Frederick D Soski
(74) *Attorney, Agent, or Firm* — Rodney J. Fuller; Booth Udall Fuller, PLC

(57) ABSTRACT

Gas flow control valves comprising a valve housing including a cylindrical interior passage, and a housing opening extending from the interior passage through the housing. The gas flow control valve further comprises a cylindrical rotary valve element including a sidewall, and a rotary valve element opening extending through the sidewall. The valve element is rotatably received within the interior passage of the valve housing, such that the housing opening may be selectively aligned with the rotary valve element opening, and an area of overlap of the housing opening and the valve element opening may be varied by rotating the valve element within the interior passage of the valve housing.

4 Claims, 11 Drawing Sheets

(51) Int. Cl.
*F16K 11/085* (2006.01)
*F16K 37/00* (2006.01)
*A61M 16/00* (2006.01)
*A61M 16/20* (2006.01)
*A61M 16/08* (2006.01)

(52) U.S. Cl.
CPC ...... *F16K 37/0033* (2013.01); *F16K 37/0041* (2013.01); *A61M 16/0045* (2013.01); *A61M 16/0825* (2014.02); *A61M 16/205* (2014.02)

(56) References Cited

U.S. PATENT DOCUMENTS

| | | | | |
|---|---|---|---|---|
| 2,641,280 A * | 6/1953 | Fleischhauer | ........ | A01G 25/162 137/624.14 |
| 2,655,929 A * | 10/1953 | Herold | ........ | B08B 9/28 134/131 |
| 2,723,102 A | 11/1955 | Mueller | | |
| 3,190,584 A * | 6/1965 | Gire | ........ | B64C 29/0091 137/625.46 |
| 3,558,100 A * | 1/1971 | Hulsey | ........ | F16K 5/10 251/207 |
| 3,692,041 A * | 9/1972 | Bondi | ........ | F02C 7/22 137/238 |
| 3,874,413 A * | 4/1975 | Valdez | ........ | F16K 11/072 137/625.47 |
| 3,941,154 A * | 3/1976 | Bishop | ........ | B05B 17/08 137/624.13 |
| 4,501,295 A * | 2/1985 | Williams | ........ | F16K 11/166 137/599.08 |
| 5,056,505 A * | 10/1991 | Warwick | ........ | A61H 9/0078 601/44 |
| 5,179,978 A * | 1/1993 | Simms | ........ | B41F 31/08 137/563 |
| 5,343,893 A * | 9/1994 | Hogan | ........ | A61G 7/05776 137/624.13 |
| 5,474,102 A * | 12/1995 | Lopez | ........ | F16L 41/03 137/271 |
| 5,517,800 A * | 5/1996 | Brenner | ........ | F16K 11/085 137/625.11 |
| 5,524,822 A * | 6/1996 | Simmons | ........ | B05B 17/08 137/625.11 |
| 6,113,483 A * | 9/2000 | Schambre | ........ | B60H 1/00028 454/121 |
| 6,708,690 B1 * | 3/2004 | Hete | ........ | A61M 16/0096 128/204.18 |
| 8,905,076 B2 * | 12/2014 | Jorgensen | ........ | F16K 11/0856 123/41.08 |
| 2003/0127096 A1 * | 7/2003 | McAuliffe | ........ | A61M 16/00 128/204.18 |
| 2006/0249153 A1 * | 11/2006 | DeVries | ........ | A61M 16/0057 128/204.18 |
| 2007/0107787 A1 | 5/2007 | Moretz | | |
| 2007/0148016 A1 * | 6/2007 | Crawford, Jr. | ........ | F04B 23/06 417/415 |
| 2007/0181185 A1 | 8/2007 | Clark | | |
| 2008/0017347 A1 * | 1/2008 | Chung | ........ | F24F 3/1411 165/4 |
| 2008/0099092 A1 | 5/2008 | Hasko | | |
| 2010/0186744 A1 * | 7/2010 | Andrieux | ........ | A61M 16/10 128/204.23 |
| 2011/0011079 A1 * | 1/2011 | Kamen | ........ | F02G 1/043 60/520 |

* cited by examiner

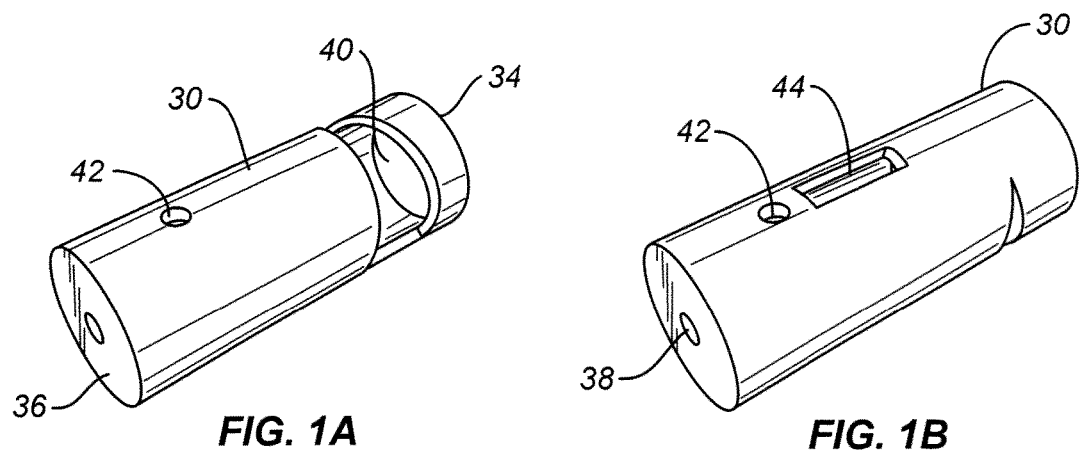
FIG. 1A    FIG. 1B
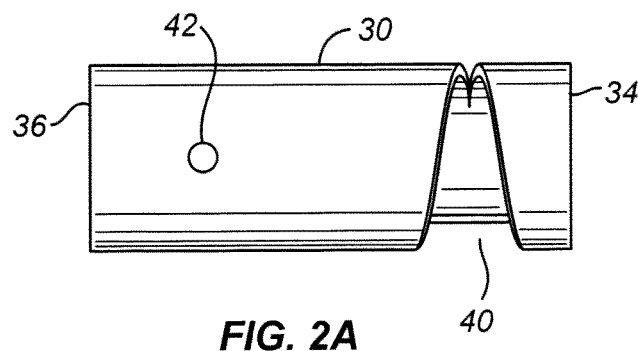
FIG. 2A
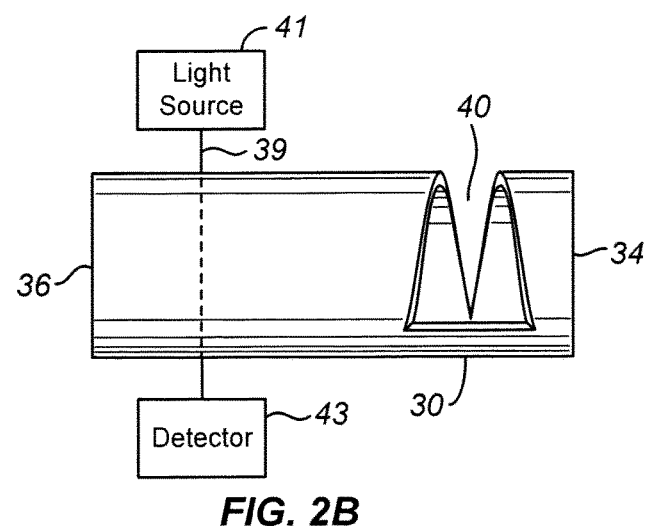
FIG. 2B

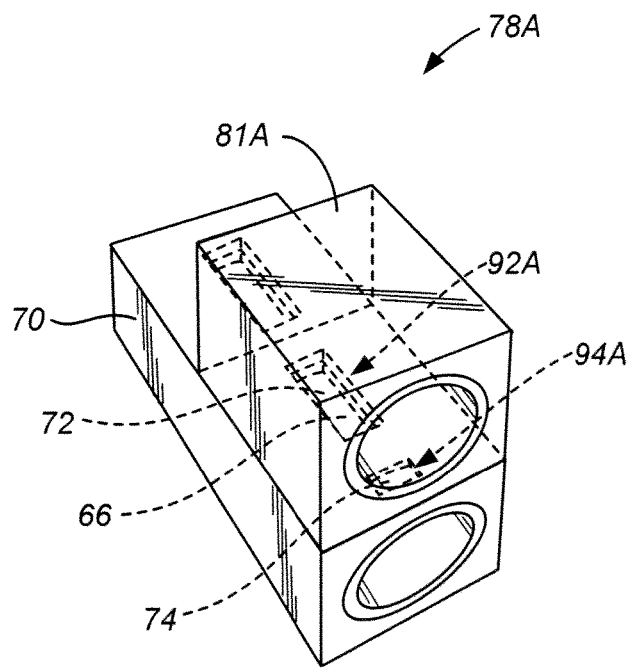
FIG. 16
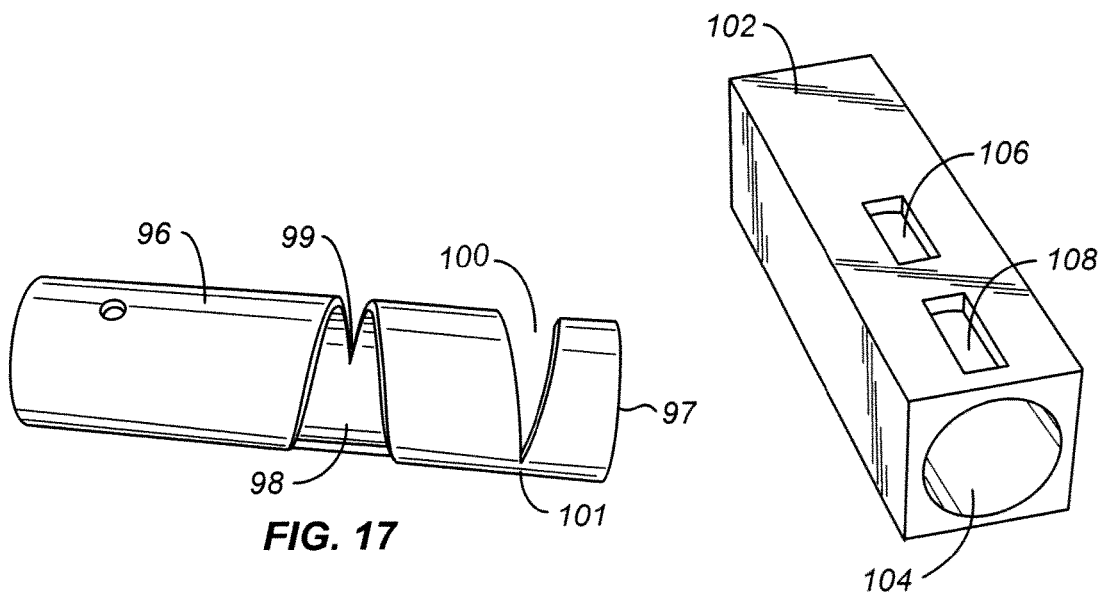
FIG. 17
FIG. 18

VARIABLE ORIFICE ROTARY VALVES FOR CONTROLLING GAS FLOW

CROSS-REFERENCE TO RELATED APPLICATION

This application is the U.S. National Stage of International Application No. PCT/US2012/025062, filed Feb. 14, 2012, which claims priority from U.S. Provisional Application Ser. No. 61/442,915, filed Feb. 15, 2011, the entire contents of each of which are hereby incorporated by reference in their entireties.

TECHNICAL FIELD

The present disclosure relates to valves for regulating or controlling the flow of gases.

BACKGROUND

Potential drawbacks to known valves include limited ability to i) provide fine control over the flow restriction; ii) provide relatively linear control of the flow; iii) achieve fast response time from fully closed to fully open without excessive power consumption; iv) be easily controlled electronically; v) control flow over a very wide range of flow rates; vi) function without lubrication; vii) in ventilation applications involving blowers, enable diversion of airflow to an exhaust port when the valve is closed, and viii) control flows at very low pressures, such as in ventilation applications, due to the size of the orifice opening required.

Two types of known valves are globe valves and piston valves. These valves are common, but suffer from a few problems, including size, slow response time, and high restriction even for low pressure drops, which creates a high pressure drop at low flows. Specifically, for ventilator applications, the same valve cannot be used for adult patients as for neonates, because the flow ranges are very different and the resolution of control at low flow rates is low.

Other types of known valves are sliding valves and other rotating valves such as plug valves, ball valves, and butterfly valves. These valves suffer from slow response time and imprecise flow control. They are good for applications requiring a simple on/off flow control, but their flow restriction is non-linear as the valve opens and closes. They are thus unable to provide proportional flow control. Another problem with these valves is that, usually, in order to enable complete sealing they require lubrication for the moving parts.

SUMMARY

The various embodiments of the present valves have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One embodiment of the present gas flow control valves comprises a valve housing including a cylindrical interior passage, and a housing opening extending from the interior passage through the housing. The gas flow control valve further comprises a cylindrical rotary valve element including a sidewall, and a valve element opening extending through the sidewall. The valve element is rotatably received within the interior passage of the valve housing, such that the housing opening may be selectively aligned with the valve element opening, and an area of overlap of the housing opening and the valve element opening may be varied by rotating the valve element within the interior passage of the valve housing.

In certain embodiments, the housing opening and the valve element opening comprise a first housing opening and a first valve element opening, respectively, and the embodiments further comprise a second housing opening extending from the interior passage through the housing and a second valve element opening extending through the sidewall.

In certain embodiments, the first and second valve element openings are circumferentially spaced from one another so that when the first housing opening and the first valve element opening are partially or fully aligned with one another the second housing opening and the second valve element opening are not even partially aligned with one another, and vice versa.

In certain embodiments, the first and second valve element openings are circumferentially spaced from one another so that rotation of the valve element in a first direction within the housing gradually increases an area of overlap between first valve element opening and the first housing opening while gradually decreasing an area of overlap between second valve element opening and the second housing opening, and rotation of the valve element in a second direction opposite the first direction within the housing gradually decreases an area of overlap between first valve element opening and the first housing opening while gradually increasing an area of overlap between second valve element opening and the second housing opening.

In certain embodiments, the first and second valve element openings are axially spaced from one another.

In certain embodiments, the first housing opening and the second housing opening are differently sized from one another, and the first valve element opening and the second valve element opening are differently sized from one another.

Certain embodiments further comprise a third housing opening extending from the interior passage through the housing and a third valve element opening extending through the sidewall.

In certain embodiments, at least one of the valve element opening and the housing opening is tapered.

In certain embodiments, the valve element opening comprises a first valve element opening, and the embodiments further comprise a second valve element opening extending through the sidewall, wherein the first and second valve element openings are located at a same axial position along a length of the valve element.

In certain embodiments, the axial position of the first and second valve element openings corresponds to an axial position of the housing opening along a length of the housing.

In certain embodiments, the valve element is open at a first end and closed at a second end opposite the first end.

In certain embodiments, the valve element is closed at both ends.

In certain embodiments, the housing opening is much larger than the valve element opening so that rotating the valve element within the interior passage of the valve housing enables flow through the valve element opening to be blocked, and also enables the valve element to change a direction of flow outward from the housing opening.

In certain embodiments, the valve element and/or the interior passage of the valve housing comprises a low-friction polymer.

In certain embodiments, the valve element comprises graphite.

In certain embodiments, the interior passage of the valve housing comprises glass.

Certain embodiments further comprise a first pair of diametrically-opposed alignment apertures in the sidewall of the valve element.

Certain embodiments further comprise a second pair of diametrically-opposed alignment apertures in the housing positioned to align with the first pair of diametrically-opposed alignment apertures when the valve element is in a home orientation.

BRIEF DESCRIPTION OF THE DRAWINGS

The various embodiments of the present valves now will be discussed in detail with an emphasis on highlighting the advantageous features. These embodiments depict the novel and non-obvious valves shown in the accompanying drawings, which are for illustrative purposes only. These drawings include the following figures, in which like numerals indicate like parts:

FIG. 1A is a perspective view of a rotary valve element or cylinder employed in a variable orifice valve in accordance with one embodiment of the present disclosure, showing the inlet and the tapered outlet slot of the cylinder;

FIG. 1B is a perspective view of the cylinder of FIG. 1A, showing the bypass orifice of the cylinder;

FIGS. 2A, 2B, and 2C are elevational views of the cylinder of FIGS. 1A and 1B, showing the cylinder in its several rotational positions;

FIG. 16 is a perspective view of a selector module in use in conjunction with the valve of FIGS. 9 and 10;

FIG. 17 is an elevational view of a rotational valve element or cylinder for use in a variable orifice flow control valve in accordance with another embodiment of the present disclosure;

FIG. 18 is a perspective view of a housing in which the cylinder of FIG. 17 is installed to form a valve in accordance with this embodiment;

DETAILED DESCRIPTION

The drawings and their descriptions may indicate sizes, shapes and configurations of the various components. Such depictions and descriptions should not be interpreted as limiting. Alternative sizes, shapes and configurations are also contemplated as within the scope of the present embodiments. Also, the drawings, and their written descriptions, indicate that certain components of the apparatus are formed integrally, and certain other components are formed as separate pieces. Components shown and described herein as being formed integrally may in alternative embodiments be formed as separate pieces. Further, components shown and described herein as being formed as separate pieces may in alternative embodiments be formed integrally. As used herein the term integral describes a single unitary piece.

The present variable orifice valves are configured and operable to regulate or control the flow of gases. In one example application, the valves can control the flow of respiratory gas (e.g. air, oxygen-enriched air, or oxygen) through a medical ventilator to deliver a desired pressure and/or volumetric flow rate to a patient. More generally, the valves disclosed herein have numerous applications for controlling the flow of any gas(es). For simplicity, the following discussion will assume that the gas flowing though the valve is air. Accordingly, the following discussion should not be considered limiting insofar as it focuses on applications for controlling gas flow.

FIGS. 1A-5 illustrate one embodiment of a variable orifice gas flow control valve 10 (FIGS. 3, 4A, 4B) in accordance with the present disclosure. The description of FIGS. 1A-5 relates to a medical ventilator application for the valves in accordance with the present disclosure. However, the valves disclosed herein are not limited to a medical ventilator application. They may be used in a variety of other applications, including, without limitation, mixing a plurality of gases, controlling flow in a vehicle heating/cooling system, etc.

Figure 2C:
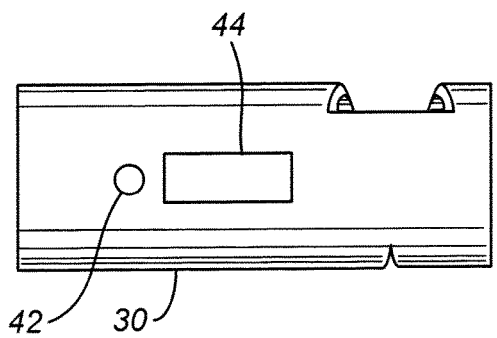
Figure 3:
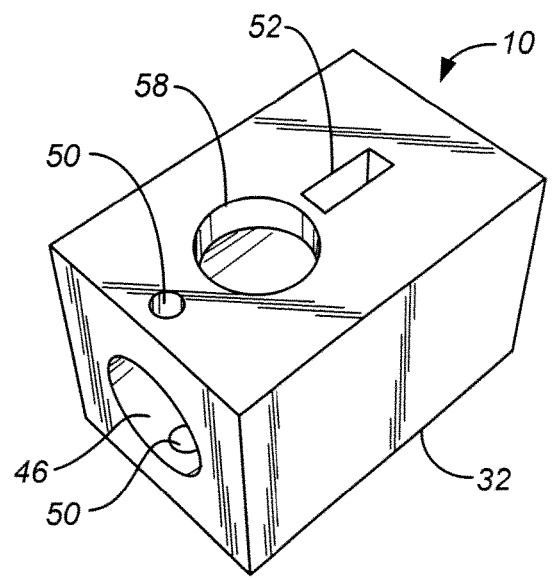
FIG. 3 is a top perspective view of a valve housing in accordance with one embodiment of the present disclosure.
Figure 4A:
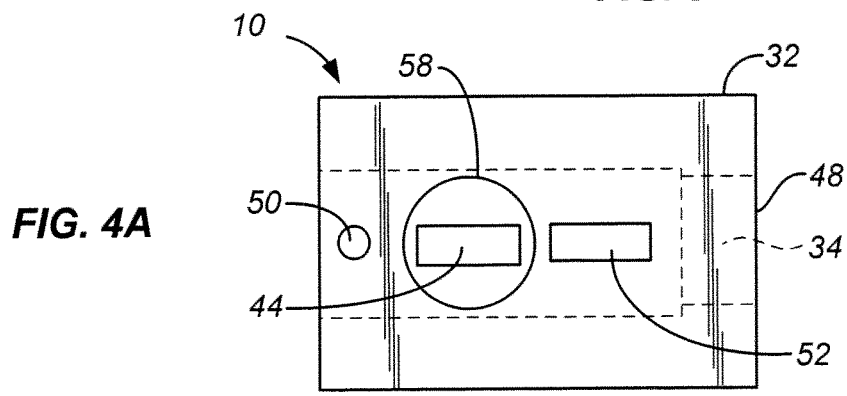
FIG. 4A is a top plan view of a valve in accordance with one embodiment of the present disclosure, the valve comprising the cylinder of FIG. 1A disposed within the valve housing of FIG. 3, showing the cylinder in a first position defining a closed variable outlet orifice closed and an open bypass port.
Figure 4B:
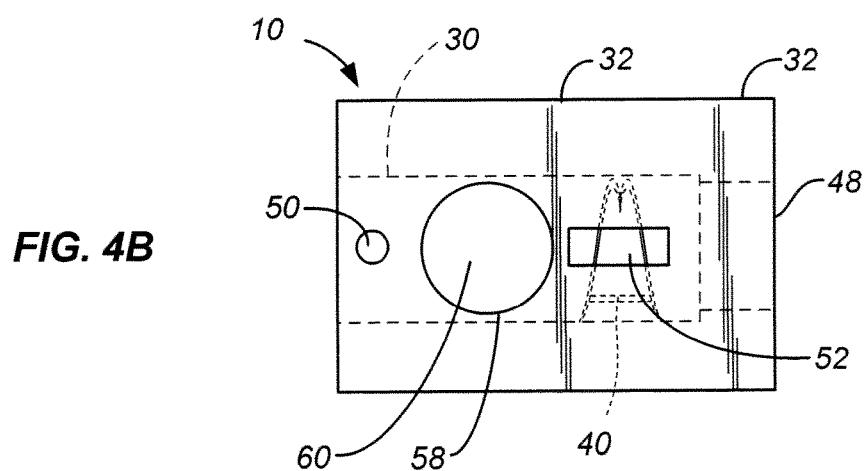
FIG. 4B is a top plan view of the valve of FIG. 3, showing the cylinder in a second position defining a partially-opened variable outlet orifice and a closed bypass port.
Figure 5:
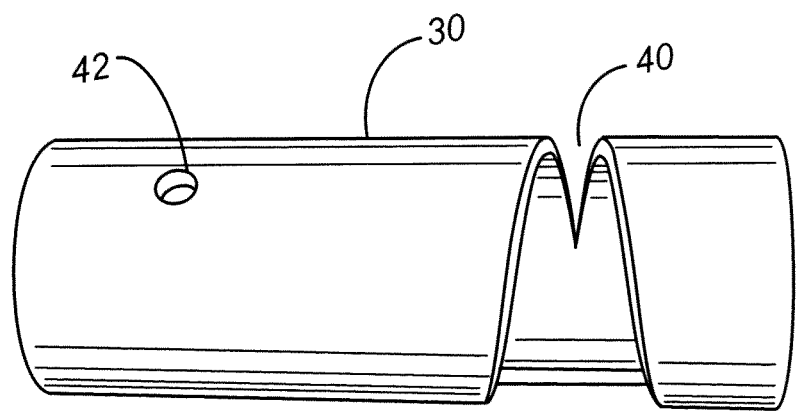
FIG. 5 is another perspective view of the cylinder of FIGS. 1A and 1B.

The valve 10 includes a generally cylindrical rotary valve element or "cylinder" 30 that is rotatably received within a housing 32 (FIGS. 3, 4A, 4B). With reference to FIGS. 1A, 1B, 2A, 2B, and 2C, the cylinder 30 is hollow, having an opening forming a gas inlet 34 at a first end, and closed at a second end 36 opposite the inlet 34. A recess or fitting 38 in the closed second end 36 receives a motor shaft (not shown) to rotate the cylinder 30 within the housing 32. In certain embodiments, the cylinder 30 may be made of graphite. However, in other embodiments the cylinder 30 may be any suitable material, such as a suitable polymer, especially a durable, low-friction polymer such as polytetrafluoroethylene (PTFE).

Adjacent the inlet 34, the sidewall of the cylinder 30 includes a first opening, cutout, or slot 40. The first opening, cutout, or slot 40 extends around a portion of the cylinder's circumference, and has a tapering width measured in the longitudinal direction of the cylinder 30. The tapered cutout 40 provides a variable orifice for a gas outlet port, as described further below. In the illustrated embodiment, the taper of the cutout 40 has a linear profile. However, in alternative embodiments the taper may have any profile, such as exponential, logarithmic, parabolic, etc. In still further embodiments, the first cutout 40 may not be tapered, and may be, for example, rectangular or any other shape. For simplicity, the first cutout 40 is referred to as a tapered cutout 40, but this terminology should not be interpreted as limiting.

In some embodiments of the valve in accordance with this disclosure, a first pair of diametrically-opposed alignment apertures 42 may optionally be provided in the sidewall of the cylinder 30, such as between the cutout 40 and the second end 36. The alignment apertures 42 define a "home" position for the valve. A beam of light 39 from a source 41 external to the valve 10 can be directed through both alignment apertures 42 to a photo-detector 43 to determine that the cylinder 30 is in the "home" orientation, as shown in FIG. 2B, which shows an orientation of the cylinder 30 in which the alignment apertures 42 face the source 41 and the photo-detector 43. The structure and/or size of the alignment apertures 42 may vary according to accuracy requirements. In other embodiments, alternative means of homing may be used, such as a magnetic (Hall effect) sensor, a photointerrupter, an encoder with a zero position, etc.

The sidewall of the cylinder 30 further includes a second opening, cutout, or slot 44, which may, in some embodiments, be configured as a rectangle. In certain embodiments, the second opening 44 of the cylinder 30 forms an exhaust or bypass opening together with a corresponding opening (described below) in the housing, as described further below. In some applications there may be no need for an exhaust or bypass opening. Thus, although the second opening 44 is referred to herein as an exhaust opening 44, that terminology should not be interpreted as limiting. Also, in some applications the size or shape of the exhaust opening 44 may vary, and may be, for example, non-rectangular. The exhaust opening 44 could be, for example, tapered.

With reference to FIG. 3, the housing 32, in one embodiment, may be a generally rectangular parallelepiped including a cylindrical passage 46 for receiving the rotatable cylinder 30. In other embodiments, the shape of the housing 32 may be other than the example configuration shown in the drawings. The passage 46 is dimensioned to prevent substantial leakage of gas between the cylinder 30 and the housing walls defining the passage 46. In certain embodiments, the passage 46 may include a lining (not shown) to reduce friction with the rotatable cylinder 30. In certain embodiments, the lining may be glass, and may fit in a tight tolerance to a graphite rotatable cylinder 30. Glass and graphite provide a long working life with low friction without the need for lubrication, while maintaining good sealing.

The passage 46 is open at both ends, including an air inlet end 48 corresponding to the gas inlet end 34 of the cylinder. In those embodiments that include the alignment apertures 42 in the cylinder 30, the housing 32 includes a second pair of alignment apertures 50 that are diametrically opposed relative to the passage 46. The housing alignment apertures 50 are positioned to align with the corresponding alignment apertures 42 in the cylinder 30 when the cylinder 30 is in the "home" orientation, so that a beam of light passing through the aligned apertures 42, 50 can be detected, as described above, to detect the home position. In FIG. 3 the closed end 36 of the cylinder 30 has been omitted so that both openings 50 in the housing 32 are visible. The apertures 42, 50 may be located anywhere on the cylinder 30 and the housing respectively. Further, the homing method including the beam of light as described is merely one possibility. Alternative methods for homing the cylinder 30 include, but are not limited to, other optical methods, magnetic (Hall effect) sensors, etc.

The housing 32 further includes a first opening 52, which is referred to herein as a gas outlet port 52, which terminology should not be interpreted as limiting. The outlet port 52 is located so as to align axially with the tapered cutout 40 of the cylinder 30 when the cylinder 30 is installed in the housing 32. The tapered cutout 40 thus provides a variable orifice for the outlet port 52 as the cylinder 30 is rotated in the housing 32, as best shown in FIGS. 4A and 4B. Due to the variable width of the tapered cutout 40 of the cylinder 30, the rotational position of the cylinder 30 within the passage 46 controls the effective area of the outlet port 52, as best shown in FIG. 4B. The ability to adjust the effective area of the outlet port 52 by rotating the cylinder 30 with respect to the housing 32 enables the volumetric gas flow rate through the outlet port 52 to be closely controlled. Because the tapered cutout 40 does not extend completely around the cylinder 30, the cylinder 30 can be rotated to an orientation in which the outlet port 52 is completely closed. In this configuration, gas can exit the valve through an exhaust or bypass opening, as described below.

With reference to FIGS. 3, 4A, and 4B, the housing further includes a second opening 58 positioned between one of the homing apertures 50 and the outlet port 52. The second opening 58 may comprise an exhaust or bypass port 58 in certain embodiments. However, the terms exhaust port 58 or bypass port 58 should not be interpreted as limiting, as the second opening 58 may have other applications, or may not be used at all.

When the cylinder 30 is installed in the housing, the exhaust opening 44 of the cylinder is axially aligned with the exhaust port 58 to form an exhaust or bypass passage. The relative positions of the tapered cutout 40 and the exhaust opening 44 on the cylinder 30 are selected so that when the tapered cutout 40 at least partially registers with the outlet port 52 (i.e. when the outlet port 52 is at least partially open), the exhaust opening 44 of the cylinder 30 is not rotationally aligned with the exhaust port 58, so that the exhaust port 58 is closed by the solid wall of the cylinder 30. When the tapered cutout 40 of the cylinder 30 is not registered with the outlet port 52 (i.e. when the outlet port 52 is closed), the exhaust opening 44 of the cylinder 30 registers with (is rotationally aligned with) the exhaust port 58, thereby opening the exhaust port 58 to provide an exhaust or bypass passage for gas flowing therethrough. This feature enables the valve to be compatible with those medical ventilators that use blowers, so that the airflow through the valve is maintained, even when the outlet port 52 is completely closed. The size and shape of the exhaust passage can be configured so that the blower will be controlled at its best operating point.

The foregoing description of the embodiment of FIGS. 1A-S assumes that the direction of gas flow through the valve is as described. However, in alternative embodiments, the direction of gas flow could be reversed. Thus, the outlet port 52 would become a gas inlet, and the inlet end 34 of the cylinder would become an outlet.

The present valves can be actuated with a manual knob (not shown) or with a variety of different motors (not shown) attached to the fitting 38 at the closed end 36 of the cylinder 30. Example motors include, without limitation, stepper motors, open loop motors, servo motors (brushless or brushed, with or without encoder) and D.C. brushed motors. A servo motor without an encoder may use some other zero positioning system and may use time and/or other parameters, such as flow rate or pressure, for the control loop. The structure of the valves enables very small and lightweight valves to be made, which are very easily controlled by stepper motors. The selection of a motor may depend upon the particular application for the valve. Also, when selecting a motor it may be desirable for the motor to be capable of high revolutions per minute (RPM), fine resolution, and/or quick response time. For example, if the valve is to be used with a medical ventilator, it is advantageous for the motor to be able to quickly ramp up from no flow (to the patient) to peak flow. Thus, it would be advantageous to select a motor that provides quick response time and high RPM. Also, in a medical ventilator application, it would be advantageous to select a motor that provides high resolution so that the flow through the valve can be precisely controlled to provide a desired pressure control or volumetric flow control. In various embodiments, flow sensors and/or pressure sensors can be provided to control the motor in accordance with techniques (such as servo control mechanisms) that are well known, for example, in the field of medical ventilators.

The present valves exhibit numerous advantages. For example, the valves enable extremely flexible control. The size (area) of the outlet port can be adjusted through 300° or more of rotation, enabling very fine adjustment. The sizes of the tapered cutout and the corresponding opening in the housing determine the minimum flow restriction (maximum flow rate), enabling very low pressure drop at high flow rates.

The shape of the taper on the cutout determines the relationship between the change in volumetric flow rate and the change in rotational angle of the cylinder. For example, the effective area of the outlet port, and thus the volumetric flow rate through the outlet port at a given pressure, may vary linearly with the rotational angle of the cylinder, or semi-linearly, or with varying degrees of resolution for different angles. In the latter example, the cutout may, for example, transition from its maximum width to 20% of its maximum width in the first 100° of rotation, and then from 20% of its maximum width to closed in the remaining 200°. This type of variable taper provides finer control in the region of high restriction (200° for 20% overall change).

The structure of the present valves enables rotation in one direction, such as clockwise, for starting at a low flow rate (minimal cutout width) and moving to a higher flow rate (wider cutout width), or vice versa. This functionality affects the response time of the valve from closed to open, as very little movement is required to transition from closed to fully open. For example, the cylinder may rotate only 20° in a first direction from closed to fully open while still providing 300° or more of rotational movement for control. However, if it is desired to gradually transition from closed to fully open, the cylinder can be rotated in the opposite direction.

When used in connection with a medical ventilator, the valve illustrated in FIGS. 1A-5 is not likely to be used at high pressures. Thus, selection of proper materials enables low inertia, fast response and very long life without lubrication. For example, in one embodiment the housing may be glass, or include a glass lining in the cylindrical passage 46, and the cylinder may be graphite. Both materials are inexpensive and they have matching temperature coefficients. Temperature will thus have a small effect on tolerances, keeping the air leak negligible with little to no friction and wear.

Figure 6:
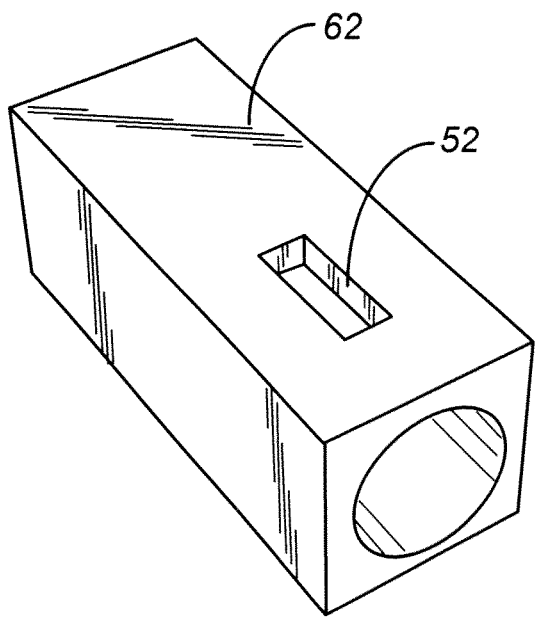
FIG. 6 is a perspective view of an alternative embodiment of the valve housing.

FIGS. 6, 7A, 7B, and 7C illustrate an embodiment of the present disclosure that does not include an exhaust or a homing mechanism in the valve itself. FIG. 6 illustrates an alternative housing 62, which is similar to the housing 32 of FIGS. 3, 4A, and 4B, but without the alignment apertures 50 or the exhaust port 58. The housing 62 of FIG. 6 thus does not provide the homing function described above, and does not enable a bypass flow of exhaust gas. A cylinder for use with the housing 62 may similarly omit alignment apertures and/or an exhaust port. A valve including the housing 62 of FIG. 6 would be most suitable for use in applications that do not need an exhaust port, that do not need a homing function, or that utilize some other form of homing mechanism not integrated into the valve itself. In an alternative embodiment, one or the other of the alignment apertures or the exhaust port may be omitted, while the other is retained.

Figure 7A:
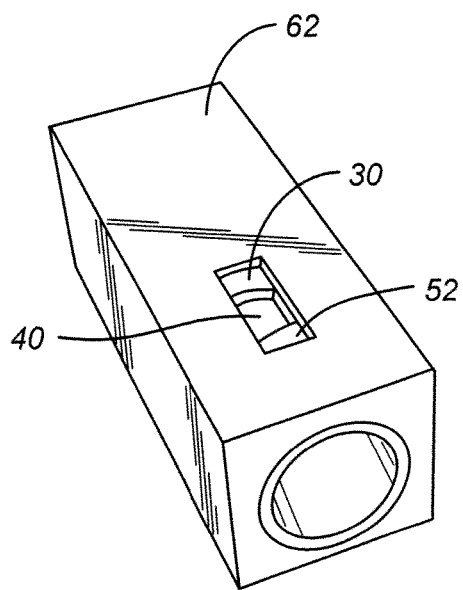
FIGS. 7A, 7B, and 7C are perspective views of a variable orifice flow control valve incorporating the housing of FIG. 6, showing the valve in first, second and third operational positions, respectively.
Figure 7B:
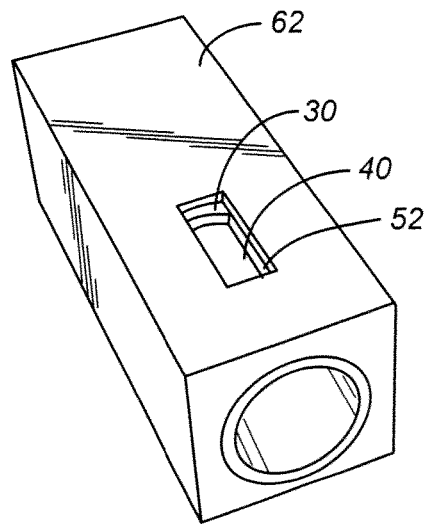
Figure 7C:
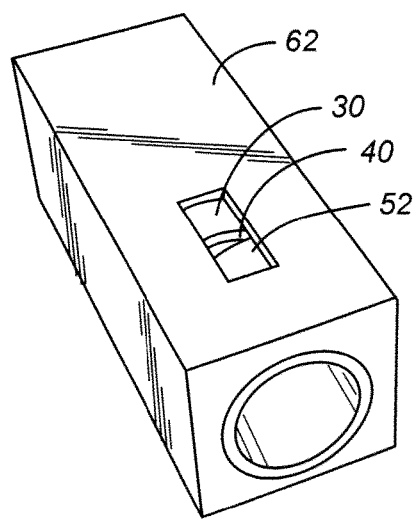

FIGS. 7A-7C illustrate the cylinder 30 rotatably disposed within the housing 62 at three different rotational positions. In FIG. 7A the rotational position of the cylinder 30 aligns an intermediate width portion of the tapered cutout 40 at the outlet port 52, enabling a moderate flow rate through the valve. In FIG. 7B the rotational position of the cylinder aligns a wide portion of the tapered cutout 40 at the valve outlet, enabling a high flow rate through the valve. In FIG. 7C the rotational position of the cylinder aligns a narrow portion of the tapered cutout 40 at the valve outlet, enabling a low flow rate through the valve.

In certain embodiments, including some discussed below, two or more tapered cutouts or slots may be provided in a single cylinder to provide multiple variable-orifice outlets, with each outlet having its own flow characteristics, thereby providing a separate operational modality for each gas outlet. For example, in a medical ventilator application, one tapered slot or cutout could provide an outlet for use with adult patients, while a second tapered slot could provide an outlet for neonates and/or infants, who typically require lower flows and higher restriction ranges. These embodiments may include an actuator or selector to select which outlet is connected to the patient.

Figure 8:
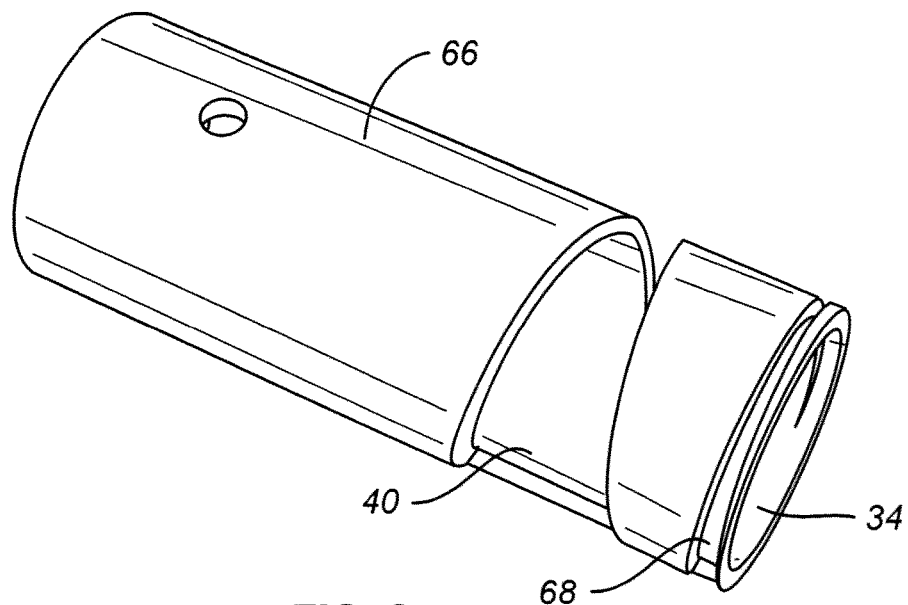
FIG. 8 is a perspective view of a rotary valve element or cylinder for use in a variable orifice valve in accordance with a second embodiment of the present disclosure.

A multi-cutout cylinder 66 for use in a multi-outlet variable orifice flow control valve in accordance with a second embodiment of this disclosure is illustrated in FIG. 8. The cylinder 66 is provided with a second tapered slot or cutout 68 in addition to the first tapered slot or cutout 40. The second cutout 68 is axially spaced from the first cutout 40 along the length of the cylinder 66. The second cutout 68, in this example embodiment, may advantageously have a more gradual taper than the first cutout 40, giving it a narrower width than the first cutout. In a medical ventilator application, the first cutout 40 may be configured to provide desired flow rates and restriction ranges for adults, while the second cutout 68 may be configured to provide desired flow rates and restriction ranges for infants and/or neonates, who generally require lower flows and higher restriction ranges. The different tapers of the two cutouts provide these varying characteristics.

Figure 9:
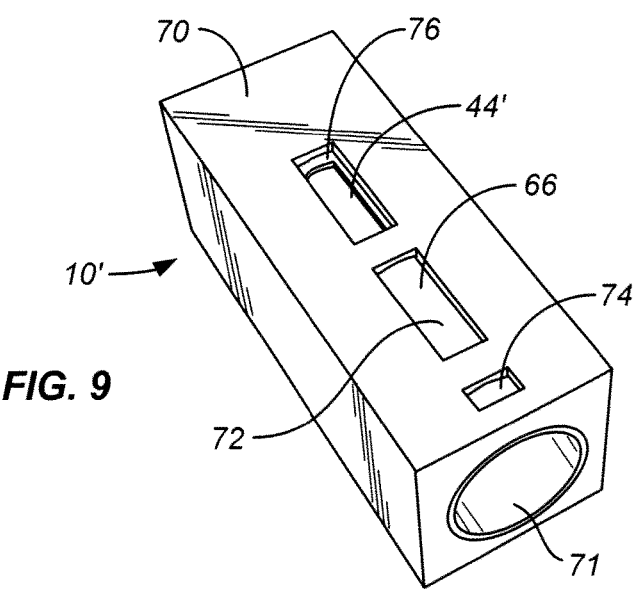
FIGS. 9 and 10 are perspective views of a variable orifice flow control valve in accordance with an alternative embodiment of the present disclosure, showing the valve in two operational positions.
Figure 10:
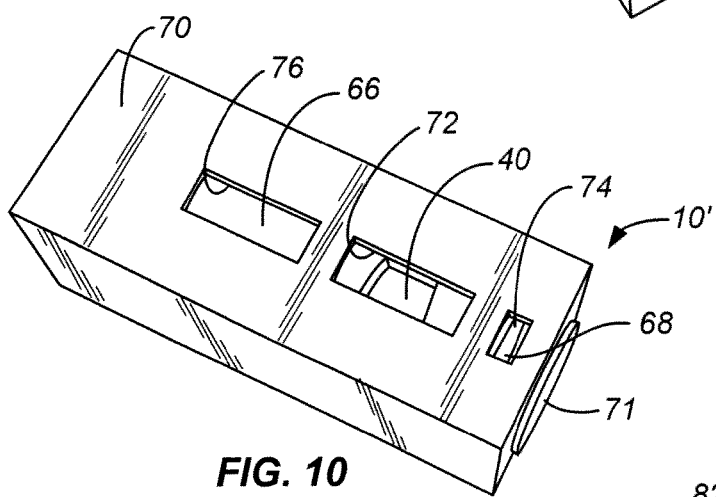

FIGS. 9 and 10 illustrate a variable orifice flow control valve 10 in accordance with the second embodiment of this disclosure, in which the cylinder 66 of FIG. 8 is rotatably disposed within a housing 70 that includes a gas inlet 71, a first gas outlet 72 and a second gas outlet 74. The gas outlets 72, 74 are axially spaced from one another, with the first outlet 72 having a location corresponding to the axial location of the first tapered cutout 40 on the cylinder 66, and the second outlet 74 having a location corresponding to the axial location of the second tapered cutout 68 on the cylinder 66 (FIG. 8). The second outlet 74 has an axial length, as measured along the longitudinal axis of the housing 70, that may advantageously be less than the axial length of the first outlet 72, reflecting the relative widths of the tapered cutouts 40, 68.

FIG. 9 illustrates the cylinder 66 in a rotational position such that the first and second outlets 72, 74 are both closed. In this orientation, an exhaust opening 44 on the cylinder 66 aligns with an exhaust or bypass port 76 in the housing to enable exhaust gas to flow out. FIG. 10 illustrates the cylinder 66 in a rotational position such that the first and second outlets 72, 74 are both open, while the exhaust or bypass port 76 is closed. Since the cylinder 66 is configured such that both tapered cutouts 40, 68 align with their respective outlet openings 72, 74 in the housing 70, it is advantageous to couple the valve of FIGS. 9 and 10 with a selector module for selecting either the first outlet opening 72 or the second outlet opening 74. In alternative embodiments, the exhaust opening 44' on the cylinder 66 and/or the exhaust or bypass port 76 in the housing may be omitted. The variable orifice flow control valve 10' may thus be operated with only the two outlets 72, 74.

Figure 8A:
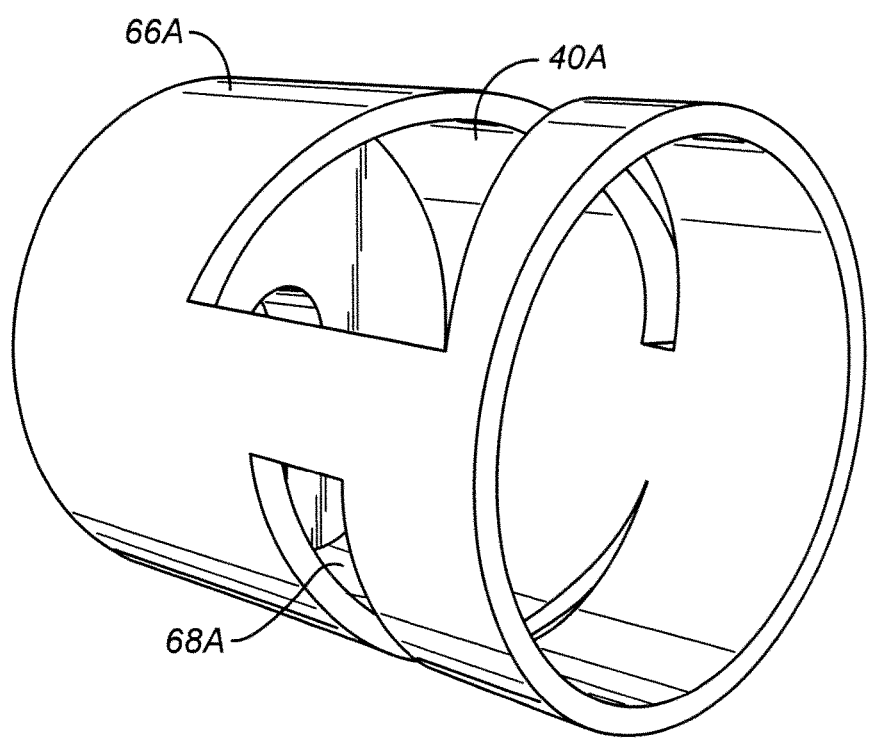
FIG. 8A is a perspective view of a rotary valve element or cylinder for use in a variable orifice valve in accordance with an alternative embodiment of the present disclosure.

As shown in FIG. 8A, in an alternative embodiment, the first and second tapered slots 40A, 68A or cutouts may be positioned at the same axial location on the cylinder 66A, with the first cutout 40A extending over a first portion of the cylinder's circumference and the second cutout 68A extending over a second portion of the cylinder's circumference. By rotating the cylinder 180 degrees, one of the of the cutouts 40A, 68A may be selectively aligned with a single opening on the housing (not shown) to select the flow range. In this embodiment, the length of each cutout 40A, 68A is limited by the length of the other cutout 40A, 68A, since the sum of the lengths of the cutouts 40A, 68A cannot exceed the cylinder's circumference. Thus, this alternative embodiment may provide less resolution than the embodiment of FIG. 8. As an example, in certain embodiments, the first cutout 40A may extend between 0°-140° and the first cutout 40A may extend between 180°-320°.

Figure 11:
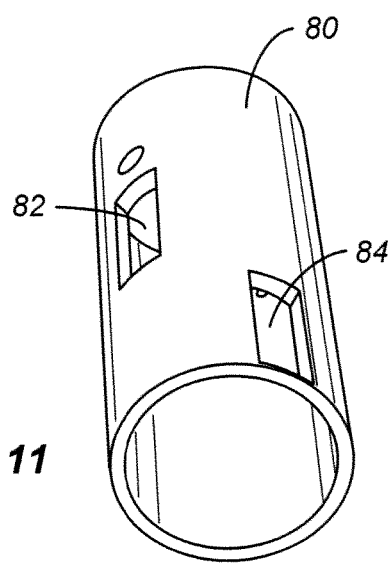
FIG. 11 is a perspective view of a selector cylinder used in an example embodiment of a selector module that may advantageously be used with the valve of FIGS. 9 and 10.
Figure 12:
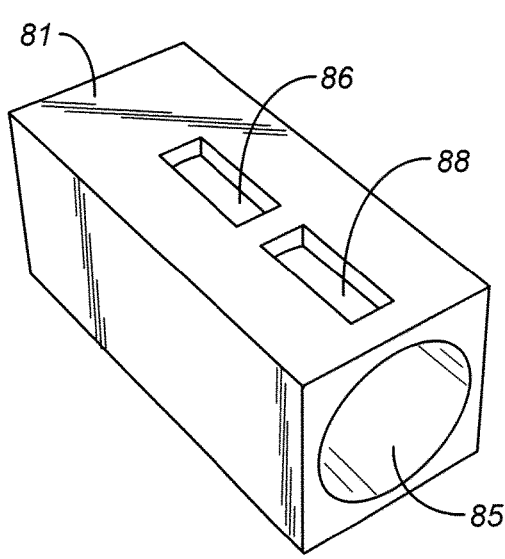
FIG. 12 is a perspective view of a housing in which the selector cylinder of FIG. 11 is installed.
Figure 13:
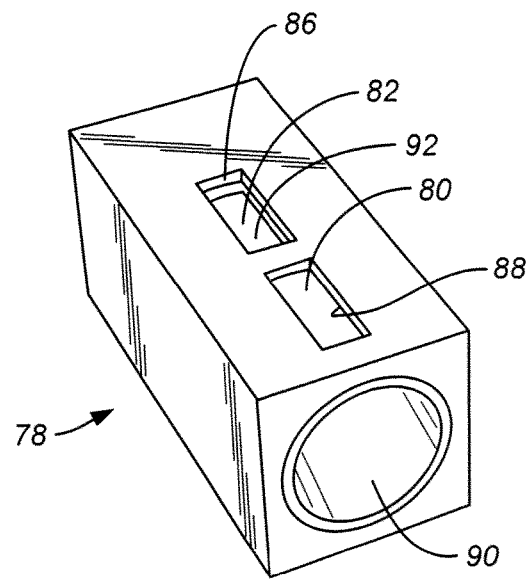
FIGS. 13-15 are perspective views of an example embodiment of a selector module comprising the selector cylinder of FIG. 11 and the housing of FIG. 12, showing the several operational positions of the module.

FIGS. 11-13 illustrate one embodiment of a selector module 78 (FIG. 13), which can be used with the valve 10' of FIGS. 9 and 10, or for other gas selection applications. With reference to FIGS. 11 and 12, the selector module includes a cylinder 80 (FIG. 11) that is installed for rotation in a housing 81 (FIG. 12) that is similar to the housing 70 shown in FIGS. 9 and 10. The cylinder 80 includes a first cutout or opening 82 and a second cutout or opening 84. The cutouts 82, 84 are spaced from one another axially along the length of the cylinder. The cutouts 82, 84 also are spaced from one another along a circumferential angular offset. The housing 81 includes an open outlet end 85, a first opening or cutout 86, and a second opening or cutout 88 axially aligned with the first opening or cutout 86, and located between the first opening 86 and the outlet end 85.

Figure 14:
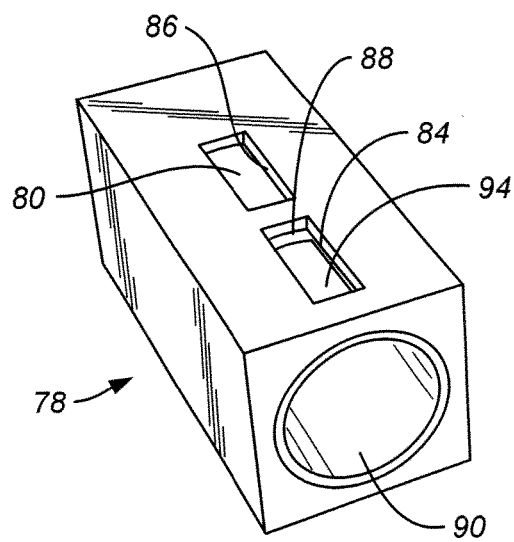

The axial positions of the cutouts 82, 84 in the cylinder 80 correspond to the axial positions of the cutouts 86, 88 in the housing 81. Thus, given the angular offset of the cutouts 82, 84 in the cylinder 80, the rotational position of the cylinder 80 relative to the housing 81 selectively aligns either the first cylinder cutout 82 with the first housing cutout 86 to form a first module inlet (FIG. 13), or the second cylinder cutout 84 with the second housing cutout 88 (FIG. 14) to form a second module inlet. Both module inlets cannot, however, be opened simultaneously. The selector module 78 can thus be used to select between a first module inlet 92 formed by the aligned first cutouts 82, 86 (FIG. 13) and a second module inlet 94 formed by the aligned second cutouts 84, 88 (FIG. 14), with an open end of the cylinder 80 and the open outlet end 85 of the housing forming a module outlet 90.

With reference to FIG. 16, a selector module 78A, which is similar to the selector module 78, can be inverted so that a first module inlet 92A aligns with the first outlet 72 in the valve housing 70, and a second module inlet 94A aligns with the second outlet 74 in the valve housing 70. The selector module 78A can thus be used to select between the valve outlets 72, 74 by changing the rotational orientation of the cylinder within the selector module housing 81A. The rotational orientation of the cylinder can be changed with, for example, a stepper motor (not shown) or a manual knob (not shown).

Figure 15:
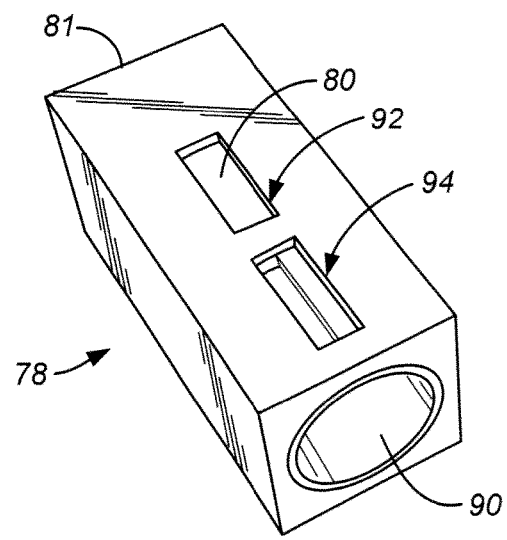

With reference to FIG. 15, the module cylinder can be rotated to provide varying degrees of partial opening of the first and second module inlets 92, 94, respectively. Thus, the degree to which the module inlets 92, 94 are selectively opened can be used to control the rate of gas flow through the selector module 78. For example, FIG. 15 illustrates the selector cylinder 80 in a rotational orientation within the housing 81 such that the second module inlet 94 is partially open. Another rotational position (not shown) of the selector cylinder 80 can provide a partial opening of the first module inlet 92. The selector module 78 can thus perform the dual tasks of selecting a single module inlet and controlling the flow rate through the selected inlet. Furthermore, the direction of gas flow through the selector module 78 can be reversed if desired, so that the module outlet 90 functions as an inlet, and the first and second module inlets 92, 94 function as first and second selectable module outlets, respectively. In alternative embodiments (not shown), the selector module may have more than two inlets that may be selectively opened and they can be tapered.

FIGS. 17-21 illustrate additional embodiments of the present valves that are particularly suited for gas mixing or blending applications. FIG. 17 illustrates a rotational valve element or cylinder 96 having an open outlet end 97, a first tapered slot or cutout 98 extending partially around the circumference of the cylinder, and a second tapered slot or cutout 100 extending partially around the circumference of the cylinder between the first cutout 98 and the open outlet end 97. The cutouts 98, 100 are axially spaced from one another, and each has the same taper profile. However, in alternative embodiments the cutouts 98, 100 could have different taper profiles. In the illustrated embodiment, the cutouts 98, 100 have reverse orientations, such that the first cutout 98 increases in width in a first circumferential direction around the cylinder 96, while the second cutout 100 decreases in width in the first circumferential direction around the cylinder 96. Furthermore, the first and second cutouts 98, 100 have respective vertices 99, 101 that are positioned on diametrically opposite sides of the cylinder 96. As further described below, the illustrated geometry of the cylinder 96 creates advantages for mixing two gases from two sources, such as air and $O_2$ in a medical ventilator application, or warm air and cold air in a vehicle heater application.

FIG. 18 illustrates a housing 102 defining a cylindrical chamber having an open end 104 for receiving the cylinder 96. The housing further includes a first inlet opening 106 and a second inlet opening 108 located between the first inlet opening 106 and the open chamber end 104. The inlet openings 106, 108 are spaced from one another along a longitudinal axis of the cylindrical chamber, and they are positioned to correspond to the axial positions of the tapered cutouts 98, 100 in the cylinder 96 when the cylinder 96 is installed in the chamber of the housing 102. A valve outlet 116 (FIG. 19) is provided by the open outlet end 97 of the cylinder 86 and the open end 104 of the housing chamber.

Figure 19:
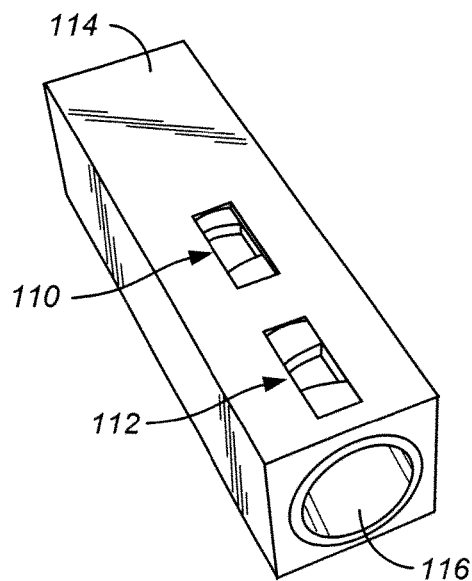
FIGS. 19-21 are perspective views of a valve in accordance with this embodiment of the present disclosure, showing the valve in its several operational positions.
Figure 20:
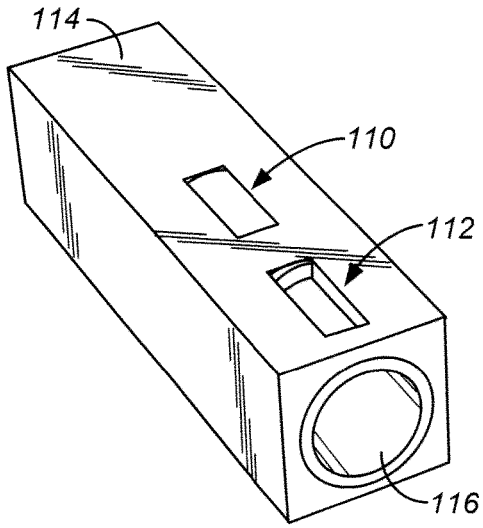
Figure 21:
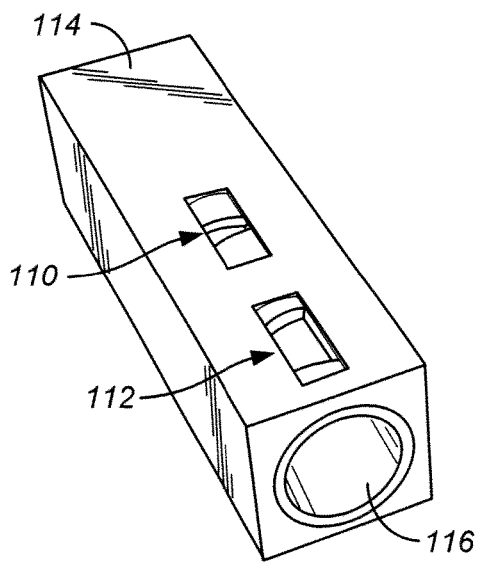

FIGS. 19-21 illustrate a variable orifice gas mixing or blending valve 114, comprising the cylinder 96 installed in the housing 102, as described above. Changing the rotational orientation of the cylinder 96 within the housing 102 enables adjustment of the flow restriction through a first inlet port 110 and a second inlet port 112 in the valve 114. The first inlet port 110 is formed by the alignment of the first cylinder cutout 98 with the first inlet opening 106 of the housing, and the second inlet port 112 is formed by the alignment of the second cylinder cutout 100 with the second inlet opening 108 of the housing 102. The mixture of gases flowing through the outlet 116 of the valve 114 can thus be adjusted by changing the rotational orientation of the cylinder 96 within the housing 104. For example, in FIG. 19, both inlet ports 110, 112 are open approximately the same amount, so that approximately equal amounts of a first gas and a second gas will be mixed inside the cylinder 96 and then exit the outlet 116. In FIG. 20, the first inlet port 110 is closed, while the second inlet port 112 is open. Thus, the gas flowing through the outlet 116 will contain only the gas flowing through the second inlet port 112. In FIG. 21, the first inlet port 110 is slightly open, while the second inlet port 112 is more fully open. Thus, the gas flowing through the outlet 116 will contain a relatively small quantity of the gas flowing through the first inlet port 110 and a relatively large quantity of the gas flowing through the second inlet port 112.

The geometry of the cylinder 96 creates advantages for mixing two gases from two sources, with one gas entering the cylinder 96 through each of the inlet ports 110, 112. Because the vertices 99, 101 of the cutouts 98, 100 are located on opposite sides of the cylinder 96, and because the cutouts 98, 100 increase in width in opposite directions around the cylinder's circumference, rotating the cylinder 96 in a first direction within the housing 102 will increase the effective orifice area of one of the inlet ports, while at the same time decreasing the effective orifice area of the other inlet port. The percentages of each gas in the mixture flowing through the outlet 116 can thus be adjusted by rotating the cylinder 96 in one direction or the other. In some embodiments the tapered cutouts 98, 100 may have different rates of taper. Example applications for such embodiments include those where the proportion of each of the constituent gases may be varied within some range smaller than 0%-100%, or where one gas is at a higher pressure than the other, which would require a smaller sized orifice for the same gas flow.

In alternative embodiments, the degree of control over the percentages of each gas in the mixture may not need to be very precise. In such embodiments the tapered cutouts 98, 100 on the cylinder 96 could be replaced with, for example, a plurality of discrete openings (not shown) having different sizes. The discrete openings could be positioned wherever needed on the cylinder to enable adjustments of the relative amounts of each gas being mixed. Furthermore, in alternative embodiments, additional inlets may be provided for mixing any number of gases. The illustrated embodiment showing mixing of two gases should not be construed as limiting.

Figure 22:
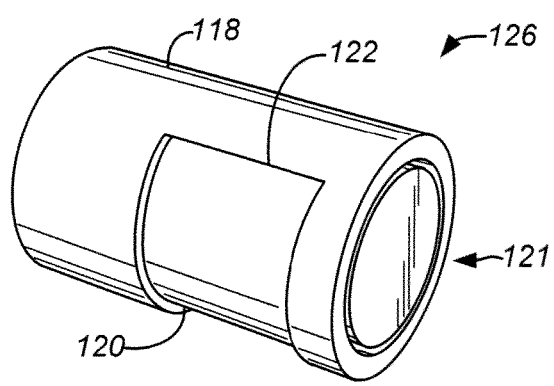
FIG. 22 is a perspective view of a variable orifice flow control valve in accordance with another embodiment of the present disclosure.
Figure 23A:
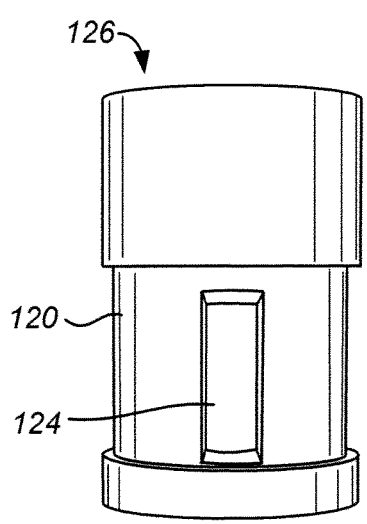
FIGS. 23A and 23B are elevational views of the valve of FIG. 22, showing the valve in its several operational positions.
Figure 23B:
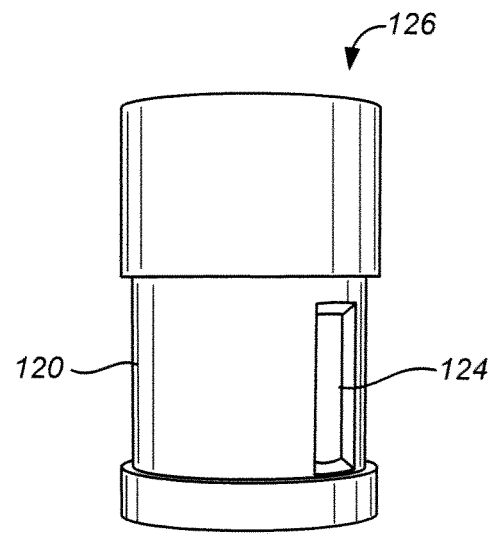

FIGS. 22, 23A, and 23B illustrate additional embodiments of the present valves that are particularly suited for directional blowing of air in room or vehicle ventilation (e.g., heating/cooling) applications. FIG. 22 illustrates a valve 126 comprising a cylindrical housing 118 that rotatably receives a cylinder 120. Both the housing 118 and cylinder 120 are open at a first end comprising an airflow inlet 121. The housing 118 includes a cutout 122 (preferably, but not necessarily, rectangular in shape) that extends over a certain percentage of the housing's circumference, for example, 50%. With reference to FIGS. 23A and 23B, the cylinder 120 includes an opening 124 (preferably, but not necessarily, rectangular in shape) that forms an airflow outlet. By rotating the cylinder 120 within the housing 118 such that the opening 124 in the cylinder 120 remains in the region of the cutout 122 in the housing, the direction of airflow through the valve 126 can be changed. Further, by rotating the cylinder 120 within the housing 118 such that the cutout 124 in the cylinder 120 is covered by the housing, airflow through the valve 126 can be blocked. The valve 126 may thus serve as not only a flow director, but also an on/off mechanism.

Figure 24:
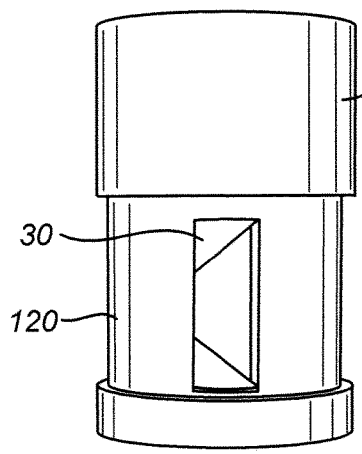
FIG. 24 is an elevational view of a variable orifice flow control valve in accordance with another embodiment of the present disclosure.

In alternative embodiments, a flow control cylinder, such as that shown in FIGS. 1A-2C, for example, may be provided inside the directional valve of FIGS. 22, 23A, and 23B. FIG. 24 illustrates such an embodiment. In this embodiment, both the direction and the amount of air flow can be controlled by the same valve system. Such an embodiment can comprise a single system direction and flow control valve for an automobile air conditioning system, for example, where the user can electronically adjust the amount of flow for a specific outlet as well as the direction of flow.

FIGS. 25-28 illustrate another embodiment of a selector module for use with the present valves. The selector module is particularly suited for use in a medical ventilator application. Thus, the following description will reference such an application. However, as will all embodiments described herein, references to particular applications should not be interpreted as limiting.

Figure 27:
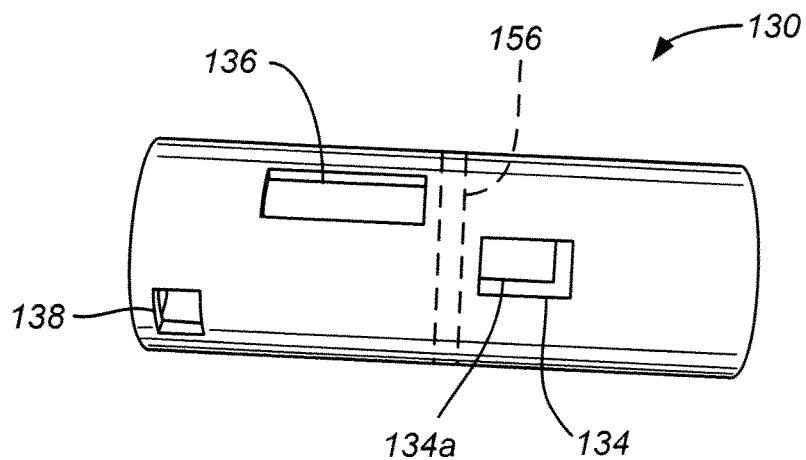
FIG. 27 is a perspective view of a cylinder for use with the housing of FIG. 25.
Figure 28:
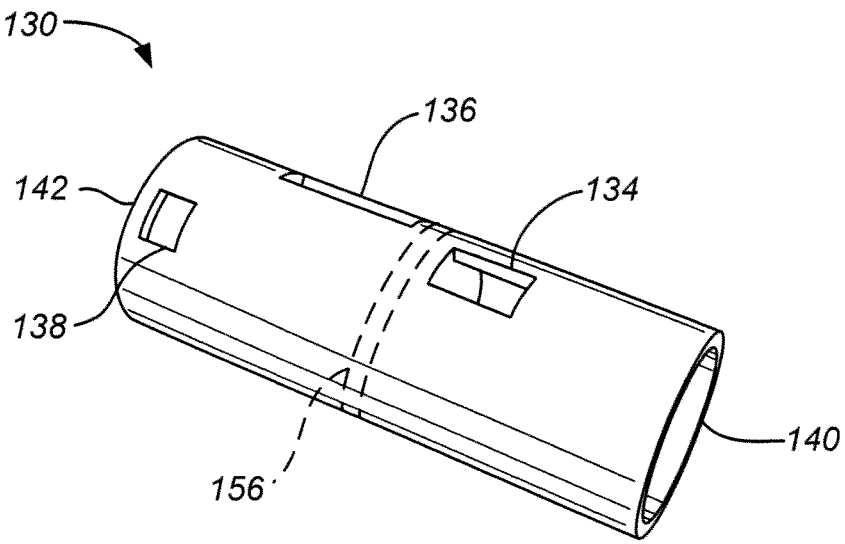
FIG. 28 is a perspective view of the cylinder of FIG. 27.

The selector module includes a cylindrical valve element ("cylinder") 130 (FIGS. 27 and 28) that is installed for rotation in a housing 132. The cylinder 130 includes a first cutout or opening 134, a second cutout or opening 136, and a third cutout or opening 138. The cutouts 134, 136, 138 are spaced from one another axially along the length of the cylinder 130. The cutouts 134, 136, 138 also are spaced from one another along a circumferential angular offset, which is described further below. With reference to FIG. 28, the cylinder 130 includes a closed end 140 and an open end 142, or flow outlet end 142. A motor or other drive apparatus (not shown) may engage the closed end 140 in a similar manner as described above with respect to the previous embodiments.

As described further below, the cutouts 134, 136, 138 correspond to cutouts or openings in the housing 132. With reference to FIG. 27, the first cutout 134 comprises an exhaust opening. The exhaust opening 134 extends diametrically through the sidewall of the cylinder 130. In other words, the exhaust opening 134 (the opening that is nearest the viewer in FIG. 27) includes diametrically-opposed cutouts 134, 134a in the sidewall of the cylinder 130. With reference to FIG. 27, the second cutout 136 comprises a first selector opening configured for adult flow rates, and the third cutout 138 comprises a second selector opening configured for neonate flow rates.

Figure 25:
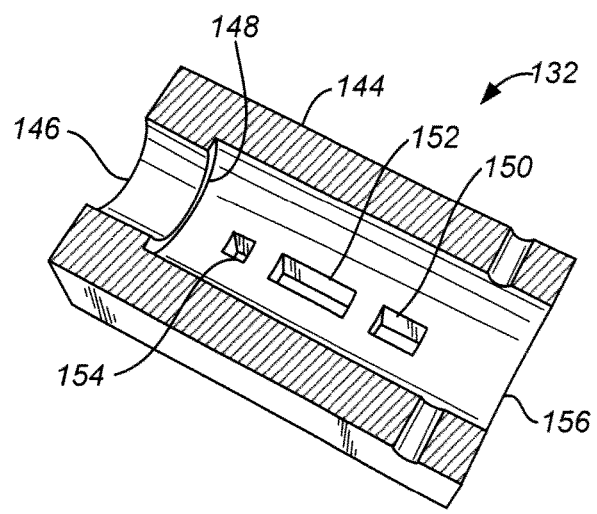
FIG. 25 is a perspective view of a first portion of a housing in accordance with another embodiment of the present disclosure.
Figure 26:
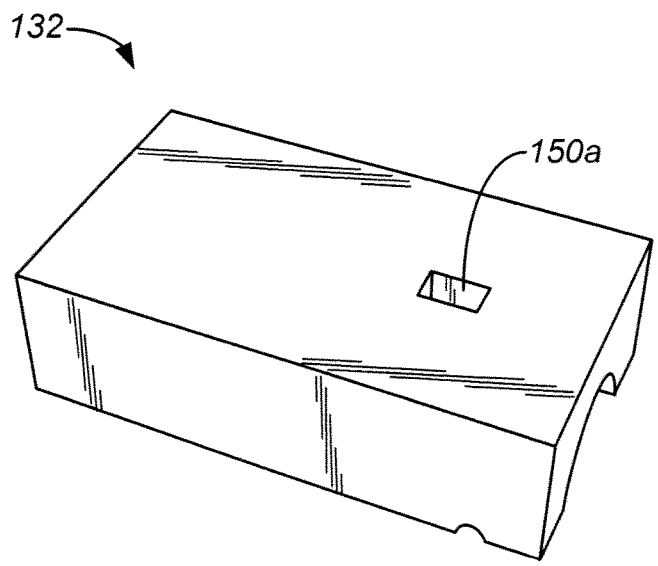
FIG. 26 is a perspective view of a second portion of the housing of FIG. 25.

FIGS. 25 and 26 illustrate the housing 132 in separate sections for ease of description. The housing can be constructed from multiple sections, or as one integral piece. The housing 132 includes a cylindrical receptacle 144 sized to receive the cylinder 130, similarly to the above-described embodiments. The receptacle 144 includes a reduced diameter at an open outlet end 146, thereby creating a transverse annular shoulder 148 against which the cylinder 130 may bear. A transverse annular shoulder may similarly be provided in any of the present embodiments.

With reference to FIG. 25, the housing 132 further includes a first opening or cutout 150, a second opening or cutout 152, and a third opening or cutout 154. The cutouts 150, 152, 154 are all axially aligned with one another and located between the outlet end 146 and a second open end 156 of the housing 132. The first opening 150 extends diametrically through opposed sidewalls of the receptacle 144. In other words, the cutout 150 in FIG. 25 includes diametrically-opposed cutouts 150, 150a in FIG. 26.

The axial positions of the cutouts 134, 134a, 136, 138 in the cylinder 130 correspond to the axial positions of the cutouts 150, 150a, 152, 154 in the housing 132. Further, the selector module is configured to abut a valve, similar to the valve 10' of FIGS. 9 and 10, so that the axial positions of the cutouts 150, 150a, 152, 154 in the housing 132 correspond to the axial positions of cutouts in the valve. The selector module can thus be used to select between adult and neonate flow rates by changing the angular orientation of the cylinder 130 within the housing 132. Given the angular offset of the cutouts 134, 134a, 136, 138 in the cylinder 130, the rotational position of the cylinder 130 relative to the housing 132 selectively aligns either the first cylinder cutout 134, 134a with the first housing cutout 150, 150a to form an exhaust outlet, or aligns the second cylinder cutout 136 with the second housing cutout 152 to form a first selector inlet for adult flow rates, or aligns the third cylinder cutout 138 with the third housing cutout 154 to form a second selector inlet for neonate flow rates. Both selector inlets cannot, however, be open simultaneously. The selector module can thus be used to select between an exhaust outlet formed by the aligned cutouts 134, 134a, 150, 150a, a first module inlet formed by the aligned cutouts 136, 152, and a second module inlet formed by the aligned cutouts 138, 154, with the open end 142 of the cylinder 130 and the open outlet end 146 of the housing forming a module outlet.

Advantageously, with reference to FIGS. 27 and 28, the cylinder 130 includes an interior partition wall 156. The partition wall 156 is located axially between the first openings 134, 134a and the second opening 136. The partition wall 156 thus further separates airflow to the patient from exhaust airflow.

Another advantage of the configuration of the cylinder is the small angular offsets between the cutouts 134, 136, 138. With reference to FIG. 27, there is very little angular separation between the first cutout 134 and the second cutout 136, and between the first cutout 134 and the third cutout 138. The angular separation between the second cutout 136 and the third cutout 138 is substantially equal to the width of the first cutout 134, which is located between the second and third cutouts 136, 138 in the circumferential direction.

The close angular spacing between the cutouts 134, 136, 138 enables fast response times. For example, a 30° rotation may move the selector from the adult setting, past the exhaust setting, to the neonate setting. A 15° stepper motor would then require only two steps to transition between the three settings. Only coarse resolution is required in such an application, as the selector module is essentially just an on/off switch. It is believed that the selector module can transition between settings in as little as 2 milliseconds.

In certain applications, smaller steps can enable a small flow to the main outlet, while most of the flow goes to the exhaust. An example of such an application where this functionality is useful is positive end-expiratory pressure (PEEP) flow in ventilation.

The selector module of FIGS. 25-28 enables a separate valve to remain at a desired setting instead of it having to move many steps to reach the proper angular orientation from its closed position. The open/close action can be performed by the selector, enabling fast transition from closed to fully open. The selector module also provides an adult/neonate selector.

The present embodiments are not limited to the structural configurations shown in the figures. In particular, certain structural features, such as locations of openings, may be reversed. For example, while FIGS. 1-4 show a tapered opening 40 in the cylinder 30, and a rectangular opening 52 in the housing 32, the opening in the cylinder could be rectangular and the opening in the housing could be rectangular. Similarly, while the openings 40, 44 in the cylinder 30 are circumferentially spaced from one another and the openings 52, 58 in the housing 32 are located on a common face of the housing 32, these configurations could be reversed, i.e. the openings in the cylinder could be located at the same circumferential position on the cylinder, while the openings in the housing could be spaced from one another in a direction perpendicular to a longitudinal axis of the housing, and could even be in separate faces of the housing.

The above description presents the best mode contemplated for carrying out the present invention, and of the manner and process of making and using it, in such full, clear, concise, and exact terms as to enable any person skilled in the art to which it pertains to make and use this invention. This invention is however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. A gas flow control system comprising:
   a blower type medical ventilator for ventilating patients; and
   a control valve for use in the ventilator, the control valve comprising:

a valve housing comprising a hollow cylindrical open-ended interior passage, and not more than one housing opening formed in a wall of said housing, wherein at least the interior passage of said valve housing is made of or lined by glass; and a cylindrical valve element comprised of graphite, the valve element comprising a valve element inlet and not more than one tapered opening in a wall thereof;

wherein the cylindrical valve element is rotatably received within the interior passage of the valve housing, such that an area of overlap of the housing opening and the tapered opening of the cylindrical valve element forms a single outlet, the size of which is varied by rotation of the cylindrical valve element within the interior passage of the valve housing, thereby obtaining a proportional flow valve; and wherein when said housing opening and said tapered opening are at least partially aligned, gas, delivered to said control valve, exits said single outlet.

2. The gas flow control system of claim 1, wherein the valve element is open at a first end and closed at a second end opposite the first end.

3. The gas flow control system of claim 1, wherein when said housing opening and said tapered opening are non-aligned and gas is delivered to said control valve, said gas flow control valve is configured to prevent gas exit.

4. A gas flow control system comprising:
a blower type medical ventilator for ventilating patients; and
a control valve for use in a ventilator, the control valve comprising:
a valve housing comprising a hollow cylindrical open-ended interior passage, and not more than one housing opening formed in a wall of said housing, wherein at least the interior passage of said valve housing is made of or lined by glass; and a cylindrical valve element comprised of graphite, the cylindrical valve element comprising a valve element inlet and a first and a second tapered opening in a wall thereof; wherein the first and second tapered openings are located at a same axial position along a length of the valve element, and wherein the second tapered opening has a narrower width than the first tapered opening;

wherein the cylindrical valve element is rotatably received within the interior passage of the valve housing, such that an area of overlap of the no more than one housing opening and the first or second tapered opening of the valve element forms a single outlet of the control valve, the size of which is varied by rotation of the cylindrical valve element within the interior passage of the valve housing, thereby obtaining a proportional flow valve whose flow range depends on which of the two tapered openings aligns with the single outlet on the housing.

* * * * *